US00PP18676P2

(12) United States Plant Patent
Vandenberg

(10) Patent No.: US PP18,676 P2
(45) Date of Patent: Apr. 1, 2008

(54) ***CHRYSANTHEMUM* PLANT NAMED 'YELLOW FICTION'**

(50) Latin Name: *Chrysanthemum×morifolium*
Varietal Denomination: Yellow Fiction

(75) Inventor: Cornelis P. Vandenberg, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 11/637,848

(22) Filed: Dec. 12, 2006

(51) Int. Cl.
*A01H 5/00* (2006.01)

(52) U.S. Cl. ..... Plt./286
(58) Field of Classification Search ..... Plt./286
See application file for complete search history.

*Primary Examiner*—Kent Bell
(74) *Attorney, Agent, or Firm*—C. A. Whealy

(57) ABSTRACT

A new and distinct cultivar of *Chrysanthemum* plant named 'Yellow Fiction', characterized by its upright plant habit; dark green-colored foliage; freely and uniformly flowering habit; daisy-type inflorescences; attractive orange and yellow bi-colored ray florets; response time about 63 days; strong peduncles; and good postproduction longevity.

1 Drawing Sheet

Botanical designation: *Chrysanthemum×morifolium.*
Cultivar denomination: 'Yellow Fiction'.

BACKGROUND OF THE INVENTION

The present invention relates to a new and distinct cultivar of *Chrysanthemum* plant, botanically known as *Chrysanthemum×morifolium,* commercially grown as a cut flower and hereinafter referred to by the name 'Yellow Fiction'.

The new *Chrysanthemum* is a product of a planned breeding program conducted by the Inventor in Bogota, Colombia. The objective of the program is to create and develop new cut *Chrysanthemum* cultivars having inflorescences with desirable floret coloration and good inflorescence form and substance.

The new *Chrysanthemum* is a naturally-occurring whole plant mutation of the *Chrysanthemum×morifolium* cultivar Coral Fiction, disclosed in U.S. Plant Pat. No. 14,653. The new *Chrysanthemum* was discovered and selected by the Inventor as a single flowering plant within a population of plants of the cultivar Coral Fiction in November, 2003, in Bogota, Colombia. The selection of this plant was based on its desirable inflorescence color and good form and substance.

Asexual reproduction of the new *Chrysanthemum* by terminal cuttings in a controlled environment in Bogota, Colombia since February, 2003, has shown that the unique features of this new *Chrysanthemum* are stable and reproduced true to type in successive generations.

SUMMARY OF THE INVENTION

Plants of the cultivar Yellow Fiction have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yellow Fiction'. These characteristics in combination distinguish 'Yellow Fiction' as a new and distinct cultivar of *Chrysanthemum:*

1. Upright plant habit.
2. Dark green-colored foliage.
3. Freely and uniformly flowering habit.
4. Daisy-type inflorescences that are about 6.8 cm to 8 cm in diameter.
5. Attractive orange and yellow bi-colored ray florets.
6. Response time about 63 days.
7. Strong peduncles.
8. Good postproduction longevity with inflorescences and foliage maintaining good substance and color for about three weeks in an interior environment.

Plants of the new *Chrysanthemum* differ from plants of the parent, the cultivar Coral Fiction, in the following characteristics:

1. Plants of the new *Chrysanthemum* flower later than plants of the cultivar Coral Fiction.
2. Plants of the new *Chrysanthemum* and the cultivar Coral Fiction differ in ray floret color as plants of the cultivar Coral Fiction have red and yellow bi-colored ray florets.

Plants of the new *Chrysanthemum* can be compared to plants of the *Chrysanthemum* cultivar Fiction, disclosed in U.S. Plant Pat. No. 12,074. In side-by-side comparisons conducted in Bogota, Colombia, plants of the new *Chrysanthemum* differed from plants of the cultivar Fiction in the following characteristics:

1. Plants of the new *Chrysanthemum* flowered later than plants of the cultivar Fiction.
2. Plants of the new *Chrysanthemum* and the cultivar Fiction differed in ray floret coloration as plants of the cultivar Fiction had purple and white bi-colored ray florets.

BRIEF DESCRIPTION OF THE PHOTOGRAPHS

The accompanying photographs illustrate the overall appearance of the new *Chrysanthemum.* These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph at the top of the sheet comprises a side perspective view of a typical flowering stem of 'Yellow Fiction'.

The photograph at the bottom of the sheet comprises a close-up view of typical inflorescences of 'Yellow Fiction'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown in Bogota, Colombia during the summer in a polyethylene-covered greenhouse and under conditions and practices which approximate those generally used in commercial *Chrysanthemum* production. During the production of the cut flowers, day temperatures ranged from 20° C. to 25° C., night temperatures ranged from 4° C. to 9° C. and light levels ranged from 3,000 to 4,000 footcandles. Measurements and numerical values represent averages for typical flowering plants. The photographs and measurements were taken when plants were about two months old from planting.

Botanical classification: *Chrysanthemum×morifolium* cultivar Yellow Fiction.

Parentage: Naturally-occurring whole plant mutation of the *Chrysanthemum×morifolium* cultivar Coral Fiction, disclosed in U.S. Plant Pat. No. 14,653.

Propagation:

*Type.*—Terminal vegetative cuttings.

*Time to initiate roots.*—About ten to 14 days with soil temperatures of about 18° C. to 21° C.

*Root description.*—Fine, fibrous; white in color.

*Rooting habit.*—Freely branching.

Plant description:

*Appearance.*—Herbaceous daisy-type cut flower.

*Flowering stem description.*—Aspect: Erect. Length: About 96 cm. Spray diameter: About 18 cm. Stem diameter: About 7 mm. Internode length: About 4 cm. Texture: Pubescent; longitudinally ridged. Color: 147B.

*Foliage description.*—Arrangement: Alternate; simple. Length: About 7.5 cm. Width: About 5 cm. Apex: Cuspidate. Base: Truncate. Margin: Palmately lobed; irregularly serrate; sinuses parallel to slightly convergent. Texture, upper and lower surfaces: Pubescent; veins prominent on lower surface. Color: Developing and fully expanded foliage, upper surface: 147A; venation, 147C. Developing and fully expanded foliage, lower surface: 147B; venation, 147C. Petiole: Length: About 1.5 cm. Diameter: About 3 mm. Texture, upper and lower surfaces: Pubescent. Color, upper and lower surfaces: 148A.

Inflorescence description:

*Appearance.*—Daisy-type inflorescence form with obovate to ligulate-shaped ray florets. Inflorescences borne on terminals, arising from leaf axils. Ray and disc florets develop acropetally on a capitulum. Uniform flowering habit.

*Fragrance.*—None detected.

*Flowering response.*—Under natural conditions, plant flower in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower about 63 days later.

*Postproduction longevity.*—In an interior environment, inflorescences and foliage will maintain good color and substance for about three weeks in an interior environment.

*Quantity of inflorescences.*—Freely flowering habit, about twelve inflorescences per stem develop.

*Inflorescence size.*—Diameter: About 6.8 cm to 8 cm. Depth (height): About 2.3 cm. Disc diameter: About 1.7 cm. Receptacle diameter: About 2.4 cm. Receptacle height: About 7 mm.

*Inflorescence buds.*—Shape: Oblate. Height: About 1.7 cm. Diameter: About 1.8 cm. Color: 8B.

*Ray florets.*—Shape: Obovate to ligulate. Surface: Slightly concave to flat. Aspect: Initially incurved; with development, about 70° to 85° from vertical. Length: About 3.8 cm. Width: About 1.2 cm. Apex: Broadly acute. Base: Fused. Texture: Smooth, glabrous; velvety; longitudinally ridged. Number of ray florets per inflorescence: About 26 arranged in about two whorls. Color: When opening, upper surface: 5A; towards the apex, 21D. When opening, lower surface: 5C. Fully opened, upper surface: 173B to 173C; towards the base, 7A. Fully opened, lower surface: 173C; towards the base, 8C.

*Disc florets.*—Shape: Tubular, elongated. Length: About 8 mm. Diameter: About 2 mm. Number of disc florets per inflorescence: About 290. Color, immature: Apex: Close to 144A. Mid-section: Close to 145B. Base: Close to 145D. Color, mature: Apex: Close to 2B. Mid-section: Close to 145B. Base: Close to 145D.

*Phyllaries.*—Quantity per inflorescence/arrangement: About 22 arranged in about two to three whorls. Length: About 1 cm. Width: About 3 mm. Shape: Elliptic. Apex: Acute. Base: Truncate. Margin: Entire. Texture, upper surface: Smooth, glabrous. Texture, lower surface: Pubescent. Color, upper surface: Close to 144A. Color, lower surface: Close to 147B.

*Peduncles.*—Length: About 16.2 cm. Diameter: About 2.5 mm. Angle: About 45° to 55° from vertical. Strength: Strong. Texture: Pubescent; longitudinally ridged. Color: Close to 148A.

*Reproductive organs.*—Androecium: Stamen number: About five per floret. Filament length: About 4 mm. Filament color: Close to 1B. Anther length: About 1 mm. Anther shape: Oblong; slender. Anther color: Close to 3A. Pollen amount: None observed. Gynoecium: Pistil length: About 7 mm. Stigma shape: Bi-parted. Stigma color: Close to 7A. Style length: About 4 mm. Style color: Close to 145B. Ovary color: Close to 157A.

*Seed/fruit.*—Seed and fruit production has not been observed.

Disease/pest resistance: Resistance to pathogens and pests common to *Chrysanthemums* has not been observed on plants grown under commercial conditions.

Temperature tolerance: Plants of the new *Chrysanthemum* have demonstrated good tolerance to low temperatures of about 4° C. and high temperatures of about 35° C.

It is claimed:

1. A new and distinct *Chrysanthemum* plant named 'Yellow Fiction' as illustrated and described.

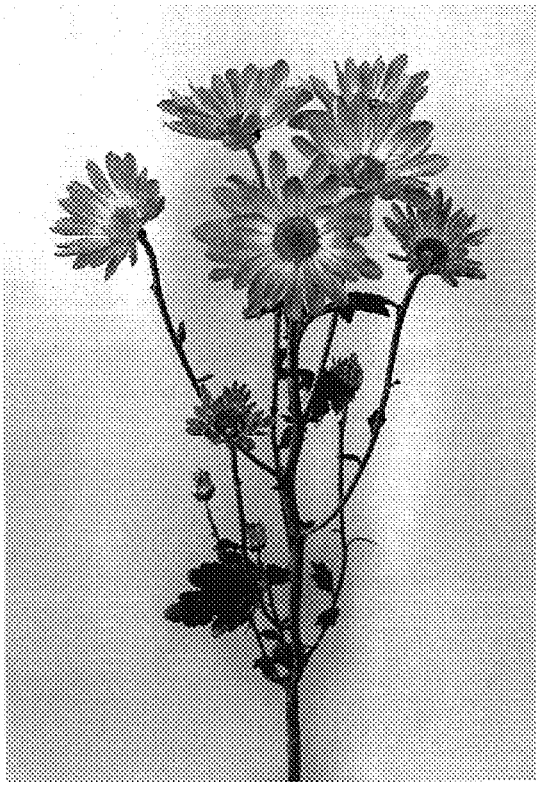
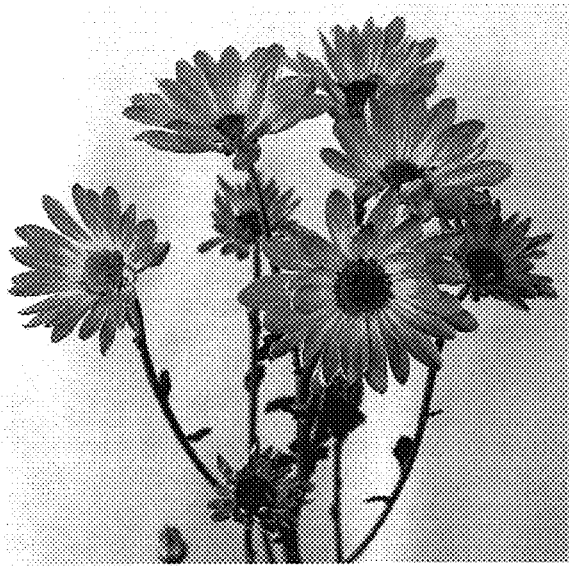

* * * * *